(12) United States Patent
Summit

(10) Patent No.: US 8,366,789 B2
(45) Date of Patent: Feb. 5, 2013

(54) PROSTHETIC LIMB

(75) Inventor: Scott Summit, San Francisco, CA (US)

(73) Assignee: 3D Systems, Inc., Rock Hill, SC (US)

( * ) Notice: Subject to any disclaimer, the term of this patent is extended or adjusted under 35 U.S.C. 154(b) by 301 days.

(21) Appl. No.: 12/128,378

(22) Filed: May 28, 2008

(65) Prior Publication Data

US 2009/0299490 A1 Dec. 3, 2009

(51) Int. Cl.
*A61F 2/60* (2006.01)
*A61F 2/78* (2006.01)
*A61F 2/80* (2006.01)
*A61F 2/62* (2006.01)
*A61F 2/64* (2006.01)
*A61F 2/66* (2006.01)
*A61F 2/68* (2006.01)

(52) U.S. Cl. ........... 623/27; 623/33; 623/39; 623/47; 623/48; 623/49; 623/50; 623/52; 623/53

(58) Field of Classification Search ........... 623/49, 623/50, 52, 33, 39, 27; 602/23, 26, 27
See application file for complete search history.

(56) References Cited

U.S. PATENT DOCUMENTS

| | | | | |
|---|---|---|---|---|
| 1,215,268 A | * | 2/1917 | Hagey | 623/49 |
| 2,490,796 A | * | 12/1949 | Gettman et al. | 623/26 |
| 4,461,045 A | * | 7/1984 | Shorter et al. | 623/40 |
| 4,608,054 A | | 8/1986 | Schroder | |
| 5,116,384 A | * | 5/1992 | Wilson et al. | 623/49 |
| 5,443,527 A | * | 8/1995 | Wilson | 623/49 |
| 5,571,207 A | | 11/1996 | Houser | |
| 6,855,170 B2 | * | 2/2005 | Gramnas | 623/49 |
| 6,942,704 B2 | | 9/2005 | Sulprizio | |
| 6,955,692 B2 | | 10/2005 | Grundei | |
| 2001/0027348 A1 | | 10/2001 | Ferrone | |
| 2003/0222366 A1 | * | 12/2003 | Stangel et al. | 264/16 |
| 2004/0236435 A1 | * | 11/2004 | Chen | 623/49 |
| 2007/0156252 A1 | | 7/2007 | Jonsson et al. | |

FOREIGN PATENT DOCUMENTS

GB 2084025 A * 4/1982

OTHER PUBLICATIONS

"International Search Report", PCT Application No. PCT/US08/07369, filed Jun. 11, 2008.

* cited by examiner

*Primary Examiner* — David Isabella
*Assistant Examiner* — Jacqueline Woznicki
(74) *Attorney, Agent, or Firm* — Dergosits & Noah LLP

(57) ABSTRACT

A prosthetic limb has an outer surface that is a mirror image of an intact limb or a generic limb design. The intact limb is scanned and the surface data is manipulated to create a virtual mirror image. If generic data is used, the intact leg can be measured and the generic surface can be adjusted so the prosthetic limb appears similar to the intact limb. The end of the amputated limb is also measured to obtain socket data. A knee and foot are incorporated to form a virtual prosthetic limb represented by design data. The design data for the virtual prosthetic limb is forwarded to a rapid prototyping machine that fabricates the entire leg simultaneously. Once completed, the prosthetic limb is shipped to the patient.

14 Claims, 13 Drawing Sheets

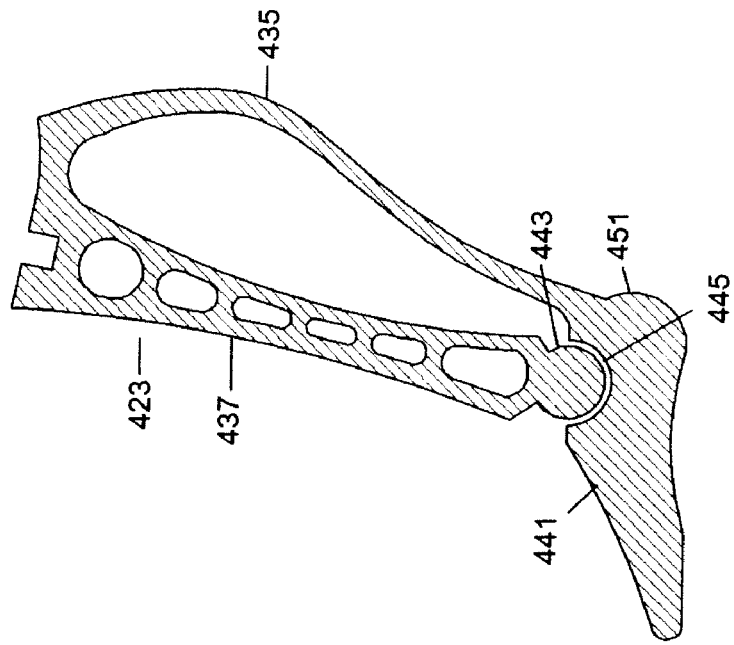
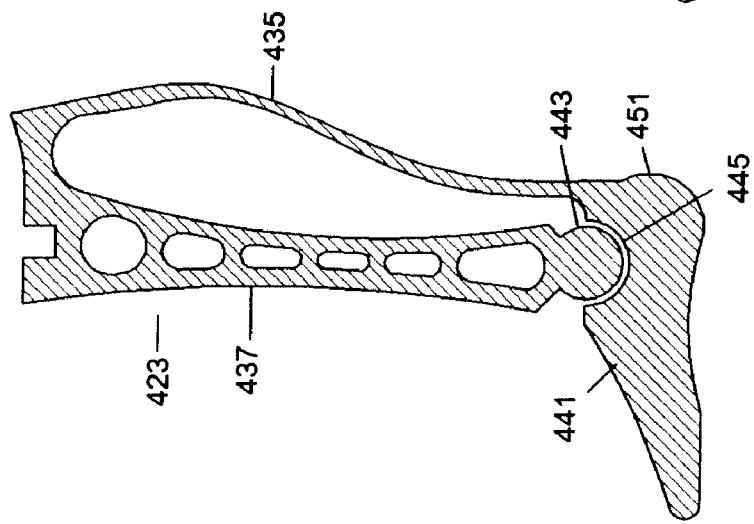
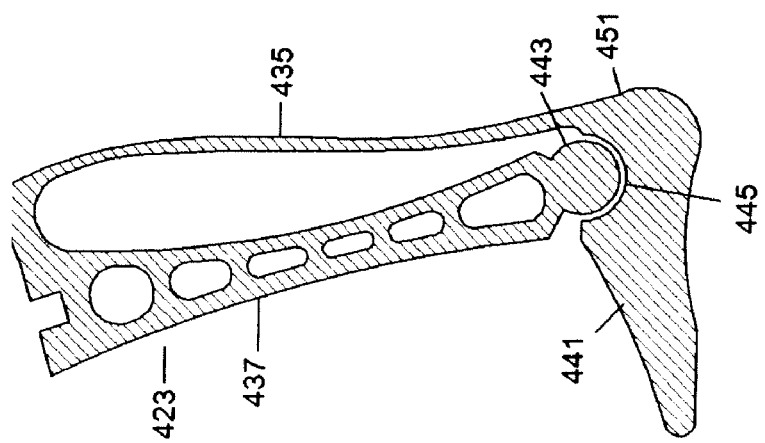

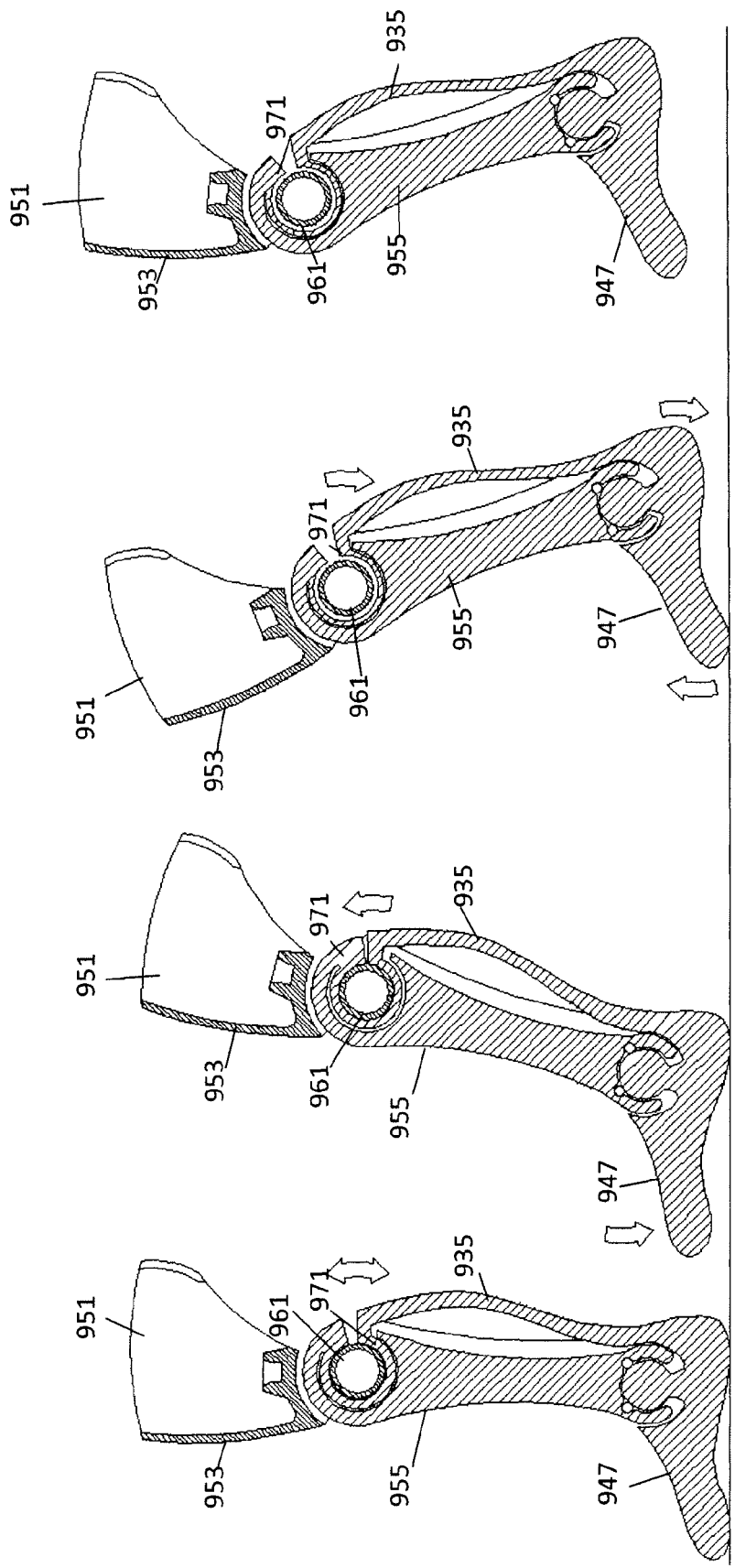

PROSTHETIC LIMB

BACKGROUND

A prosthesis limb replaces a missing extremity, such as an arm or a leg and may be needed for a variety of reasons, including diseases, and accidents. An artificial limb may also be needed when a person is born with a missing or damaged limb(s). The type of prosthesis limb used is determined largely by the extent of an amputation or loss and location of the missing limb. A transtibial prosthesis is an artificial leg that is attached to a user below the knee and includes a lower leg, ankle and foot. The transfemoral prosthesis is an artificial leg that is attached to the user's amputated limb above the knee and includes an upper leg and mechanical knee. A transradial prosthesis is an artificial arm that is attached to the user below the elbow and includes a forearm and hand. A transhumeral prosthesis is an artificial arm that is attached to the user above the elbow.

In developing areas of the world, including large portions of Africa, the leading causes of amputations are industrial, vehicular, and war related accidents. In more developed areas, such as North America and Europe, the leading causes for the amputations are diseases including cancer, infection and circulatory. In the United States, approximately 100,000 legs are lost each year to diabetes, vascular disorder, accidents and cancer. Because there are so many amputations, there is a substantial need for prosthetic limbs.

The engineering of prosthetic limbs has improved greatly. In particular, artificial knees and feet have been developed for prosthetic legs that provide increased mobility and functionality. While the engineering and mechanics of prosthetic limbs have evolved greatly, very little thought has been given to the aesthetics of the human being for whom the device was intended. With reference to FIG. 1, a modern prosthetic leg 101 is shown having a socket 121 that has a recessed surface that engages the end of the user's amputated leg. The socket 121 is typically a padded plastic structure that distributes the compression forces on the end of the amputated limb. The bottom of the socket 121 is attached to a pylon 123 which is a tubular support that can be made of titanium or aluminum. The pylon can be manufactured through an extrusion process. The bottom of the pylon 123 is attached to an artificial foot 125 that can be a molded plastic structure. The prosthetic leg 101 may also have a foam covering 127 and can be attached to the socket 121 and pylon 123 to provide a more uniform shape. The various socket 121, pylon 123 and foot 125 can be coupled together using fasteners including bolts, screws and adhesives.

A problem with the existing prosthetic limbs is that they are not readily available to people who live in remote parts of the world. Many of these people do not have access to prosthetic limb manufacturers. Also, since prosthetic limbs are very expensive, many people do not have the financial resources to purchase them. Without these resources, the amputees cannot obtain properly designed prosthetic limbs and may rely upon other devices for mobility such as crutches or wheelchairs. One shortcoming of a lower-quality leg is a knee that consists of a basic hinge. While this does allow upper and lower leg to rotate similar to a human leg, the knee does not lock out with each stride, increasing the risk of a fall or uncertain step. While these devices provide basic mobility, they are not as practical as prosthetic limbs since they require the use of arms. Thus, the user cannot use his or her arms while moving.

What is needed is a more cost effective prosthetic limb that can be built for patients with minimal equipment.

SUMMARY OF THE INVENTION

The present invention is directed towards an improved prosthetic limb that can be fabricated to match the mechanical dimensions of a user's intact limb. The prosthetic limb is created by a prosthetic designer using computer aided design (CAD) software and computer controlled fabrication processes. While the prosthetic limb is described as a leg, the same processes can be used to fabricate prosthetic arms, and as such, prosthetic arms are intended to fall within the scope of the present invention.

A prosthetic leg is created for a patient using a computer aided design system. The prosthetic leg can include an upper leg, knee, lower leg, and foot. If the user has a sound leg, a prosthetic leg having matching mechanical dimensions can be designed. In order to accurately create a matching prosthetic leg, the mechanical dimensions of the user's intact leg are first measured. The measurement of the intact leg is preferable done with an optical measuring device but any other measuring device can be used. The measuring device can be used to obtain the lengths and relative positions of the intact leg including: the foot, ankle, lower leg, knee and upper leg.

The lower leg may be coupled to the foot with a movable ankle that includes a ball joint. In an embodiment the lower leg has two members that extend from the knee to the ankle. The front member can be the primary load bearing structure that is coupled to the ball and socket ankle joint that is built into the foot. The rear member can be a flexible structure that is coupled to the front member at the top of the lower leg and the heel of the foot. When the user walks, the front member is rigid while the rear member expands and contracts as the user walks. When the heel contacts the ground, the foot rotates forward and the rear member is compressed. The front member rotates forward and the rear member extends to its normal state when the lower leg is upright and then the rear member is stretched as the lower leg rotates further forward. The elasticity of the rear member provides a spring mechanism for the foot and also allows the foot to rotate side to side.

In addition to the basic leg dimensions, the socket shape must correspond very closely to the end of the amputated limb in order for the prosthetic leg to be comfortable when worn. The socket design data is typically provided by a prosthetist. Like the leg surface data, the socket design data can be obtained through optical scanning of the end of the amputated limb. Alternatively, the end of the amputated limb can be measured manually with various mechanical measuring devices. These measurements are used to create a socket surface shape that is substantially the reversed shape of the end of the amputated limb. The socket design may also factor in padding materials that are placed between the amputated limb and the socket wall. In an embodiment, the measurements for the end of the amputated limb may also be digitized and stored in electronic memory, so both the socket and leg data can then be combined and used by the CAD system to produce an accurate prosthetic limb for the user.

The knee design is a stock data file that is selected by the designer based upon the other design parameters of the prosthetic leg. Factors can include side of leg, weight of patient, movement of intact knee, etc. A suitable knee design can be selected based upon this information. In a preferred embodiment, the knee will include multiple linkages that are coupled to the upper and lower leg. The linkages may be elongated members that are coupled to the knee by rods that rotate within holes at the ends of the linkages. The multiple linkages allow the prosthetic leg to move in a manner that replicates the movement of an intact knee. In addition to providing realistic movement, the knee can also have a locking mechanism that stabilizes the leg. For example, the knee may lock in a specific position with a locking mechanism or an automatic locking mechanism that is actuated when the leg is straightened. The locking mechanism may have a manual release that is controlled by the user or an automatic release that senses when the user moves the leg forward.

In an embodiment, the knee has a self locking mechanism that is actuated when the user applies weight to the lower leg having a front member and a rear member. The front member can be coupled to the ball and socket ankle joint that is built into the foot and the rear member can be a flexible structure that is coupled to the heal of the foot. A large diameter rod is coupled to the bottom of the upper leg and extends across the width of the knee and a "C" clamp is placed around the rod and coupled to the lower leg. One end of the C clamp is coupled to the top of the front member and a second end of the C clamp is coupled to the top of the rear member. When the rear member is compressed the C clamp is tightened around the rod locking the lower leg in place. When the user moves forward, the rear member is stretched and the C clamp is loosened which allows the lower leg to rotate relative to the upper leg. When the lower leg is lifted and the rear member is in a normal state, the C clamp may apply a slight friction against the rod which allows the lower leg to be positioned by the user but prevents the lower leg from swinging freely.

The knee and ankle of the prosthetic leg may have sliding connections at the knee and ankle. In order to minimize the friction, lubricants can be used at these connection points. Alternatively, lower friction bearings or bushings can be used at these rotating connections. In an embodiment, the bearings such as ball or roller can be placed in small indentations or recesses in the knee or ankle that function as races or sliding surfaces for the bearings. By inserting the bearings, the rotational friction due to the sliding components is reduced.

In an embodiment, the user's intact foot is scanned and used in the design of the prosthetic leg. In another embodiment, the intact foot is measured but not scanned. Rather than fabricating a mirror image foot, a stock foot design that may have a matching length and width is retrieved from a database. The retrieved design data is then integrated into the prosthetic leg design and fabricated simultaneously with the rest of the leg. In yet another alternative embodiment, the feet are stock items that are manufactured in various sizes and models. Some feet have energy storing members that allow the user to run more efficiently. Alternatively, the feet can be sized to match the intact foot which would allow a user to wear matching shoes. Digital representations of the stock feet components can be stored in a database that is accessible to the design system.

The prosthetist uses the CAD based application to combine the leg data with socket, knee and foot data to create a complete virtual prosthetic leg that is displayed on the computer. These GUI controls can allow the prosthetic designer to alter the prosthetic design in various ways to customize various attributes of the design within parameters designated by variables built that will control the leg's movement and the appearance. A GUI tool can be used, for example, to change the foot, knee and socket components used with the leg. Thus, the prosthetic designer can create a prosthetic leg that substantially matches the mechanical geometry of the intact leg.

In addition to being the proper dimensions, the prosthetic leg must also be strong enough for the required use. A prosthetic leg must be able to support the user's weight and impact while running or jumping and a prosthetic arm must be able to withstand the normal use forces. In an embodiment, the strength of the prosthetic limb is determined by the geometry of the prosthetic limb components and the materials used to fabricate the components. Suitable materials include high strength plastics such as high strength polyamide metals, alloys and composites such as carbon fiber in an epoxy binder.

The CAD system can be used to design the load bearing member of the prosthetic leg. In general, the prosthetic leg will be much stronger than required by the user. In an alternative embodiment, the prosthetic designer can input the weight and activity level of the user into the CAD system and the required strength can then calculate based upon expected loads. The CAD system can then design a load bearing structure that will be able to support the load requirements. Because the prosthetic leg is intended to be cost effective, the load bearing member is a simple solid or hollow elongated structure that supports the entire load. Alternatively, the prosthetic leg can be an elongated hollow structure that provides an external surface that corresponds to the intact leg.

Once the design is finalized, the design data produced by the CAD system can be used to fabricate the prosthetic leg. Because the information for the socket and leg are in a digital format, the patient can be in a remote location and the leg design information can easily be transmitted electronically to a prosthetic fabricator located in a more industrial area. The leg can then be fabricated using the design data and shipped to the patient located in the remote rural location.

In the preferred embodiment, the prosthetic leg is fabricated through a rapid prototyping process that uses an energy beam directed at a bath of liquid or powdered material. Similar fabrication processes are known as additive manufacturing, rapid manufacturing, layered manufacturing, 3D printing, laser sintering, and electron beam melting (EBM). These fabrication processes use an energy beam that is deflected across the material and causes the exposed material to harden. Another possible manufacturing process is fused material deposition (FDM).

The cross section design data is used by the fabrication machine to construct the main or entire leg assembly in a sequential series of layers. As each layer of material is hardened, the completed portion of the leg component is moved vertically into the bath and the next cross section layer is formed and fused to the adjacent formed layer. When all layers are formed, the leg component is completed. Because the fabrication process can be precisely controlled to create sliding surfaces, even the knee can be fabricated simultaneously with the other portions of the prosthetic leg.

In the preferred embodiment, the prosthetic leg is fabricated as a single integrated structure with the upper leg, knee, lower leg and foot all being fabricated simultaneously so that the finished product is complete. As discussed above, the moving components of the inventive prosthetic leg are coupled to the knee having rotating components. For example, the knee may have linkages or rotating components that have rods that rotate within holes. The rapid prototyping method can simultaneously produce the rods and corresponding holes most accurately when the holes and rods are formed by depositing layers of material that are perpendicular to the center axis. Thus, the layers are sequentially formed and perpendicular to the center axis of the holes and rods. The knee rotates about an axis that is substantially perpendicular to the length of the leg and parallel to the ground, thus the holes and rods will be aligned across the width of the knee. Since the entire leg is fabricated simultaneously, the layers that form the leg will be sequentially formed from one side of the leg to the opposite side.

In another embodiment, the leg may have one or more replaceable stock components that can be added or replaced after fabrication. For example, the foot may be a stock component that is attached to the lower leg. Similarly, the socket may be removable or adjustable so that the socket can be modified as the end of the user's amputated limb changes.

BRIEF DESCRIPTION OF THE DRAWINGS

The invention will be more fully understood by reference to the following detailed description of the invention in conjunction with the drawings:

FIGS. 4a, 4b, 4c are cross section views of a lower leg and foot of a prosthetic leg in different positions;

FIGS. 7a, 7b, 7c and 7d illustrate a cross sectional view of the prosthetic leg having a locking knee in different positions;

DETAILED DESCRIPTION

The present invention is a custom designed prosthetic limb having an integrated construction. The inventive prosthetic limb is primarily directed towards prosthetic legs but the same design and fabrication processes can also be used to create prosthetic arms. The prosthetic limb is preferably designed by an industrial designer using a Computer Aided Design (CAD) program.

In an embodiment, the inventive prosthetic leg includes a load bearing component that functions as the human femur, knee, tibia and foot. The upper leg of the load bearing component is attached to a socket that engages the end of the amputated limb. The lower end of the upper leg and the upper end of the lower leg are coupled to the artificial knee. The lower end of the lower leg is coupled to an artificial foot. The mechanical data for the prosthetic leg may include the relative positions of the socket, knee and foot as well as the movement of these components based upon geometry and movement of the intact leg. The mechanical data for a patient can be provided by a prosthetist. This mechanical data is digitized and input into a CAD program that is referenced to design the prosthetic leg. An example of a suitable CAD program is Pro/Engineer by Parametric Technology Corporation. Other CAD software includes: SolidWorks by SolidWorks Corporation a subsidiary of Dassault Systèmes, S. A.

Figure 1:
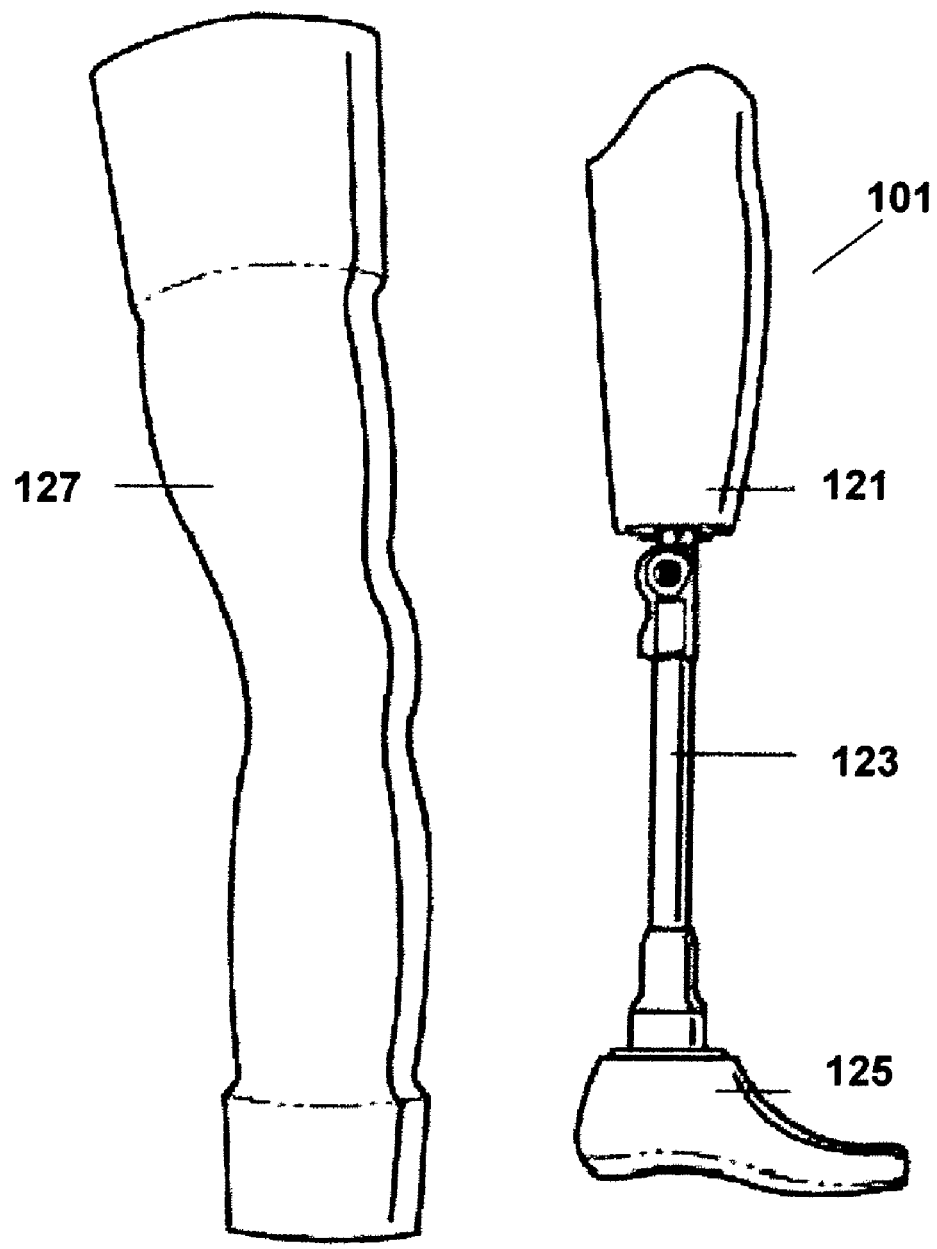
FIG. 1 is a view of a prior art prosthetic leg.
Figure 2:
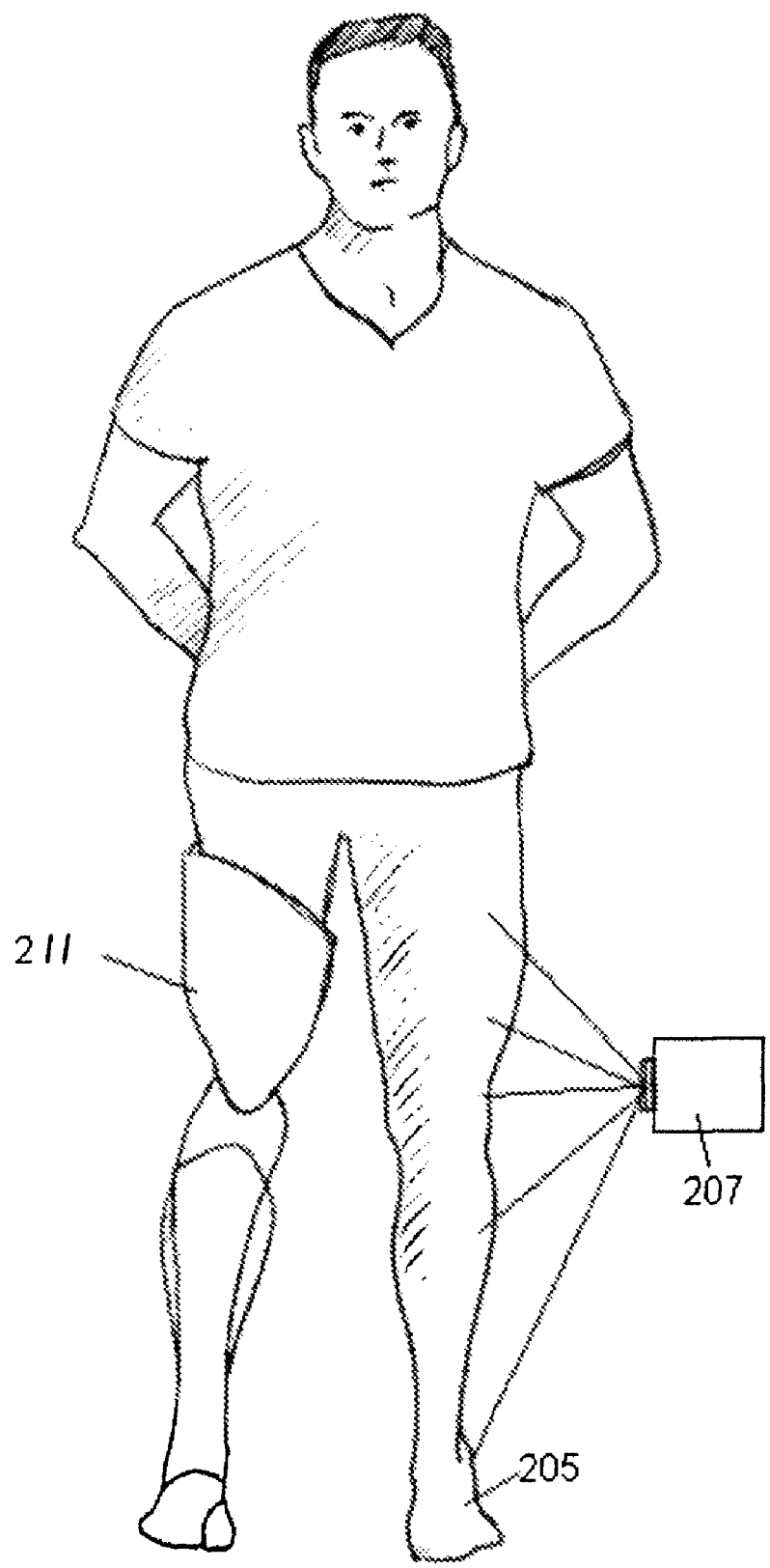
FIG. 2 is a view of a scanning device used to digitize an intact leg.

In an embodiment, the exterior surface of the prosthetic leg is a mirror image that is matched to the user's intact leg. The surface data of the intact leg can be obtained through a laser scanning process and input into the CAD program. With reference to FIG. 2, the intact leg 205 is scanned with a three-dimensional laser scanner 207. The leg 205 must be scanned from multiple sides to obtain a full three dimensional digital image. The scanner 207 creates a data set of geometric measurements for many points on the surface of the leg 205. The accuracy and detail of the three dimensional digital image is improved by taking more measurements of the leg 205. In addition to obtaining data for the intact leg 205, the described laser scanning method can also be used to obtain the surface measurement data for the end of the amputated limb 209. Photo detectors may be used to collect color information so that the exact color(s) of the intact leg 205 can be determined and used to create the prosthetic leg 211. Suitable handheld laser scanners include the FastSCAN system by Polhemus and the Handyscan 3D system by Handyscan. While optical scanning is the preferred method for determining the surface of the intact leg, in other embodiments any other optical, electromagnetic or mechanical method can be used to obtain this surface information.

While some scanning systems are capable of detecting a surface contour with a resolution less than a millimeter, the described scan does not require this level of accuracy to create a prosthetic leg that appears substantially like the outer surfaces of the intact leg. In an embodiment, it is possible to adapt scanning mechanisms such as bar code readers to scan the user's intact leg. Grocery store bar code readers that have been discarded and modified have been used to produce acceptable surface data that can be used to create the outer surfaces of the prosthetic leg.

The scan data is converted into a usable surface file that can be read by the CAD program. More specifically, the surface data from scan of the intact leg 205 may be referenced in order to extrapolate the shape of the intact leg 205 through a reconstruction process. The reconstruction process uses an algorithm that connects the adjacent points, known as a point cloud, with lines from the scanned leg data to construct a continuous surface from many small polygon shapes that form a polygon model. The data produced by the reconstruction process is a continuous three dimensional digital representation that closely matches the surface of the intact leg 205. The same reconstruction process can be used to obtain the surface data for the end of the amputated limb 209. An example of the software used to perform the scanner data reconstruction process is Geomagic Studio by GeoMagic and Pro Scan Tools which is a plug in module for Pro/Engineer by Parametric Technology Corporation.

The reconstruction surface file for the intact leg is input into the CAD program. The prosthetic designer can use the CAD program to reverse mirror and manipulate the intact leg data to create a mirror image digital representation. This mirror image data can then be used in the design of the exterior surface of the prosthetic leg. The leg and socket data are used to form the outer surfaces of the prosthetic leg. The sound side leg geometry is referenced in the creation of the exterior prosthetic surfaces, while the data representing the end of the amputated limb is referenced to create the socket for the upper leg.

Figure 3:
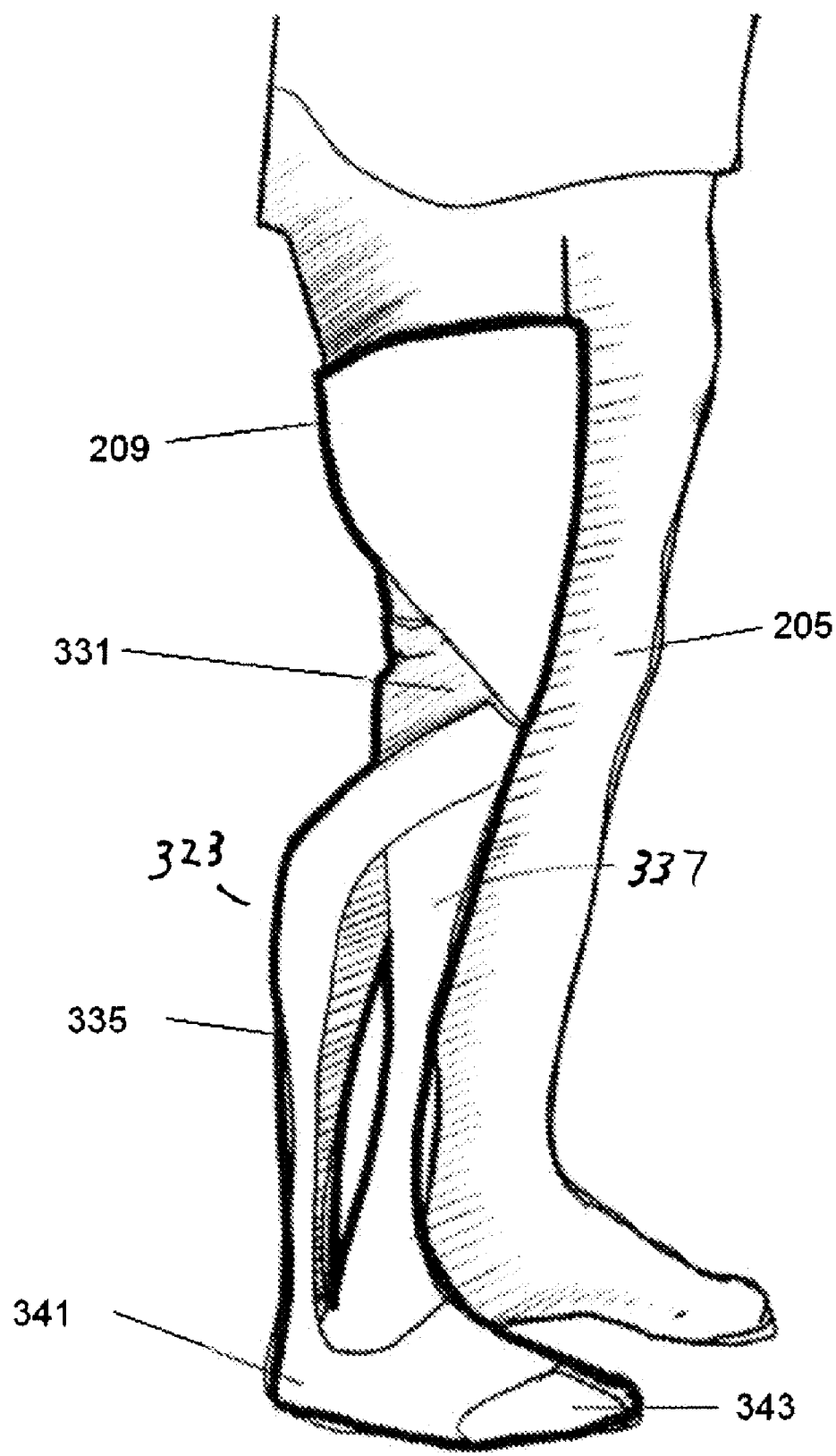
FIG. 3 is a view of a prosthetic leg.

In addition to solid physical structures, moving components are also required for a fully functional prosthetic leg including an artificial knee and ankle. With reference to FIG. 3, the user can consult with a prosthetist to determine the exact relative placement of the artificial knee 331 and foot 335 in relation to the end of the amputated limb 209. The prosthetist can use the measurement of the intact leg 205 and use this information as a starting point to determine the relative positions of the socket, artificial knee 331 and foot 335 in the prosthetic leg.

The placement of the artificial knee 331 and foot 341 relative to the end of the amputated limb 209 are specified by the prosthetist and input into the CAD program. These components can be displayed within the prosthetic leg on a computer. The CAD program can manipulate the components to enlarge, rotate, add or remove or change components and show the movement of the prosthetic leg. All internal mechanical design information can be saved in computer readable format for future modification or prosthetic fabrication. This can be particularly useful when the patient is a child who is still growing. The prosthetic data can be altered to account for the growth. Revising a stored prosthetic leg design can be easier than generating an entirely new leg.

The prosthetic leg can include inner and/or outer structural components that are used to construct the upper and lower legs. The upper and lower legs can be elongated load bearing members may have an outer surface that is load bearing and internal structures that are also load bearing. For example, the internal structure can be an elongated solid member and the outer structure can be an elongated hollow member that is a mirror image of the intact leg. The inner and outer structures can be coupled with additional members and that form a framework or lattice. In an alternative embodiment, the outer surfaces of the leg can have sufficient strength to support the required loads without any internal load bearing structures. In this embodiment, the outer surface may match or resemble the intact leg while the internal volume of the leg is an open space. The hollow spaces allow the prosthetic leg to be light weight and strong enough to support the user's weight.

With reference to FIG. 3, the lower leg 323 can also include two elongated members, a front member 337 that provides most of the strength required to support the weight of the user and a rear member 335. When the leg 205 is in the upright position, the compressive force can be distributed between the front member 337 and rear members 335. Alternatively, the front member 337 and rear member 335 can perform functions other than providing compressive strength. For example, the prosthetic designer can provide a flexible connection between the foot 341 and lower leg 323 so the foot 341 may rotate at the ankle area. The rear member 335 may be flexibly coupled to the back of the foot 341 so that the foot 341 can move in a more natural and comfortable manner. The foot 341 may also be designed to be more flexible so that it provides some cushioning while the user is walking. Since the entire leg 205 is preferably made of the same plastic material, flexibility can be designed into specific areas of the foot 341 by using thinner material cross sections that are parallel to the axis of rotation so the front of the foot 341 can bend relative to the rear foot 341. Since the plastic materials used to create the leg 205 are elastic, the bending of the foot 341 can be proportion to the forces applied to the foot 341. For example, a greater force will be applied to the foot 341 when the user is running than when walking resulting in increased bending of the flexible components.

FIGS. 4a, 4b and 4c are cross sectional views of an alternative embodiment of the lower leg 423 and foot 441. The upper ends of the front member 437 and the rear member 435 are coupled below the knee of the lower leg 423. The front member 437 extends in a substantially straight path to the foot 441 and functions as the primary load bearing structure. The bottom of the front member 437 may have a cylindrical, ball or convex spherical surface 443 which slides within a corresponding, cylindrical or spherical socket 445 in the foot 441. Thus, the front member 437 is not rigidly coupled to the foot 441. The socket 445 surrounds the upper portion of the ball surface 443 so the ball surface 443 is captured within the concave spherical socket 445 and the foot 441 is securely coupled to the lower end of the front member 437.

The rear member 435 extends from the connection with the front member 437 at the top of the lower leg 423 in a curved shape to the heel of the foot 441. The rear member 435 holds the foot 441 in place and provides a spring mechanism that allows the foot 441 to rotate relative to the lower leg 423. Because the rear member 435 is curved, the distance between the ends of the rear member 435 can be stretched or compressed elastically as the foot 441 moves relative to the front member 437. The rear member 435 is preferably much thinner than the front member 437 so that it is able to flex and control the foot 441 resistance to rotation relative to the lower leg 423. The prosthetic designer can alter the rear member 435 to provide a specific spring rate. A heavier user will require a stiffer spring rate than a lighter weight user. Similarly, a less active user may prefer a lower spring rate than an athletic user.

FIG. 4a illustrates the leg in a heel 451 forward portion with the foot 441 angled forward relative to the front member 337. The movement of the foot 441 causes the rear member 435 to be compressed which results in a larger outward bowing. FIG. 4b shows the leg in the normal straight position. The foot 441 is substantially perpendicular to the lower leg 423 and the rear member 435 is in its natural state. FIG. 4c illustrates the leg in a forward position relative to the foot 441. The ball surface 443 has rotated within the socket 445 and the rear member 435 has been stretched which causes the curvature of the rear member 435 to flatten. Since the rear member 435 is flexed elastically, when forces are not applied to the foot 441, the foot 441 will tend to return to a normal position perpendicular to the front member 437 of the leg.

The bottom of the front member 437 is a ball surface 443 which can rotate in any direction including side to side. When the user steps onto an uneven surface, the foot 441 can rotate so that the bottom of the foot 441 will adjust to the uneven surface. When the foot 441 rotates from side to side, the rear member 435 will also bend elastically to the side. The side to side spring rate of the rear member 435 can be different than the front to back movement. Since the side to side movement will cause the rear member 435 to deflect sideways, the side to side spring rate is controlled by the thickness of the rear member 435. A thicker rear member 435 will be more resistant to side to side movement than a thinner rear member 435. The thickness of the rear member 435 is preferably designed to provide side to side stability but also provide some rotational movement to allow the foot 441 to have the maximum contact area with the surface so that traction is improved and the foot 441 is less likely to slip and cause the user to fall.

Figure 5:
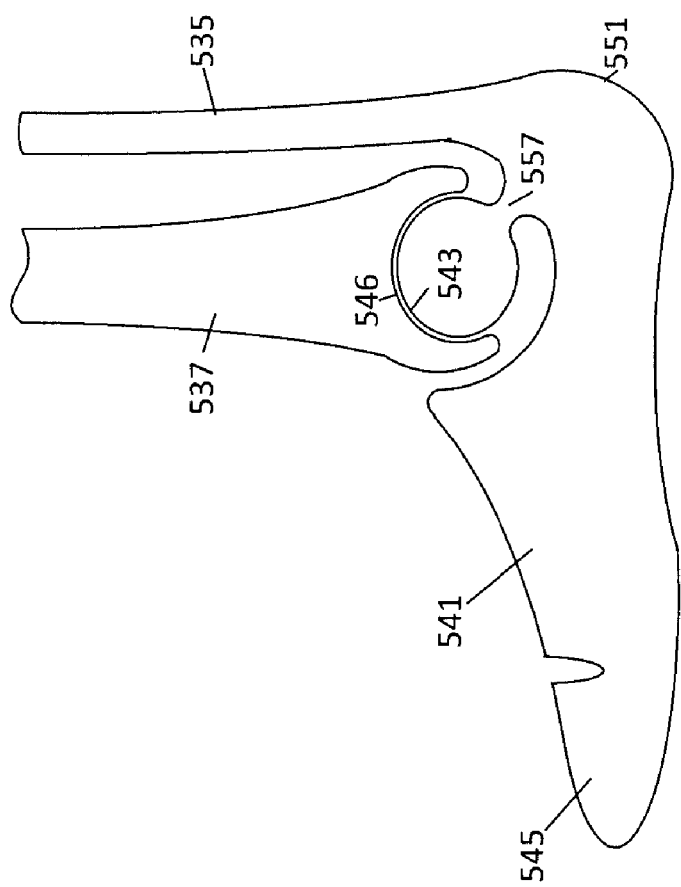
FIG. 5 is a view of an embodiment of the lower leg and foot of a prosthetic leg.

While the ball and socket connection of the leg and foot have been described with the ball at the base of the leg and the socket within the foot, it is also possible to have a different configuration. With reference to FIG. 5, the foot 541 may incorporate a ball surface 543 that is mounted to the end of a flexible post 557 which can provide additional cushioning for the user. When the foot 541 impacts against a surface, the user's body weight impacts against the leg and compresses concave spherical surface 546 of the front member 537 against the ball surface 543. Since the post 557 is not directly under the ball surface 443 and the front member 537, the impact causes the post 557 to elastically flex downward. This deflection is elastic flexing of the post 557 which cushions the impact force of the user's weight. As the lower leg rotates relative to the foot 541, the ball surface 543 may slide against a spherical socket 546 at the bottom of the front member 537. The rear member 535 is flexible but rigidly coupled to the back of the foot 541 which allows the foot 541 to move in the same manner illustrated in FIGS. 4a-4c as well as side to side. The prosthetic designer can control the spring rate of the lower leg based upon the spring rate of the post 557. A thicker post 557 can be used with heavier and more athletic users.

The artificial foot used with the prosthetic leg can also be selected from a database of feet. Like the artificial knees, digital representations of the various different sizes and shapes of feet may be available. The proper foot may also be selected for the patient by the prosthetist and the digital representation can be used in the design of the prosthetic leg. For example, the foot may be designed to be flexible so that it provides energy storage and cushioning when compression forces are applied to the heel and toe. The entire leg can be fabricated simultaneously so that the knee and foot are integrated and inseparable from the prosthetic leg. The simultaneous fabrication also allows the knee and foot to have a mechanical relationship, so that knee motion is directly influenced by foot angle. This mechanical relationship does not occur when knee and foot are fabricated independently, usually by separate manufacturers.

In addition to the movement of the foot 541 relative to the leg about the ankle, the toe portion 545 of the foot 541 can also move relative to the heel portion of the foot 541. The plastic materials used to create the prosthetic leg can be elastic and the components can be made rigid or flexible based upon their thickness at the area of bending. In an embodiment, the foot 541 can have a thin flexible section which allows the foot 541 to bend at an area where the toes 545 would normally bend. In the preferred embodiment, the toes are normally aligned with the rest of the foot 541. When the user walks and the foot 541 is being lifted so the heel 551 is raised but the front of the foot 541 is still on the surface, the area 545 may flex so that the front of the foot 541 remains in full contact with the surface. When the front of the foot 541 is separated from the surface, it will return to a normal aligned position relative to the foot 541. This feature allows the prosthetic foot 541 and leg to move in a more natural manner.

The bottom of the foot contacts the ground and provides gripping force that stabilizes the leg and makes walking with the prosthetic leg possible. In an embodiment, the user can place a shoe over the foot to provide the required traction with the ground. In other embodiments, the main foot may be made of a hard polyamide while the bottom of the foot may be an elastic rubber type material that is attached to the main foot. The elastic material provides traction and cushioning so the user does not have to wear a shoe over the foot. In an embodiment, the thickness of the foot may be configured to match the user's intact foot without shoes. The bottom of the foot includes grip areas that provide traction and resist slipping. In addition to the traction areas, an elastic layer may also be releasably attached to the bottom of the foot so that when the user is wearing a shoe on the intact foot, the layer can be attached to the foot so the length of the prosthetic leg matches the length of the intact leg and the shoe. The elastic material can be one or more pieces that can be textured to provide additional traction particularly on wet surfaces. The elastic material can be attached to the foot by elastically surrounding a portion of the foot or alternatively attached by fasteners such as straps, screws, Velcro, etc. This configuration gives the user the option of wearing a shoe on the prosthetic foot or attaching a layer to the prosthetic foot to provide matching leg lengths.

Another moving component of the inventive prosthetic leg is the knee which can be a simple hinge type coupling or in other embodiments, the prosthetic knee may have a plurality of movable linkages which mimic the complex movement of a human knee. The multi-linkage knee is designed to cause the lower prosthetic leg to move in a manner that matches the movement of the intact leg. Because the knee is a movable structure with rods that rotate within holes or bushings, the tolerances between the moving components must be very close to avoid having an unstable knee. The knee must also provide a substantial amount of strength to support the applied forces. The linkages used in the knee are preferably solid structures that pivot at each end. The strengths of the linkages can be improved by increasing their thickness or configuring the knee with multiple linkages can be arranged in parallel across the width of the knee.

The knee can be a stock design that includes a multiple linkage assembly that mimics the movement of a human knee. Different knee designs may be used for different sized patients and different types of expected use. The prosthetic designer can select an appropriate knee design based upon the user's physical characteristics including: size, weight, activity level, mobility, strength, intact knee movement, etc. The dimensions and movements of the different knee designs can be stored in a computer database. The knee designs may include a plurality of linkages that are coupled to the upper and lower leg. The knee linkages are preferably connected by rods and holes may rotate to simulate the movement of a human knee. Because the linkage rotation results in sliding friction between the components, the sliding surfaces may require lubrication.

Figure 6B:
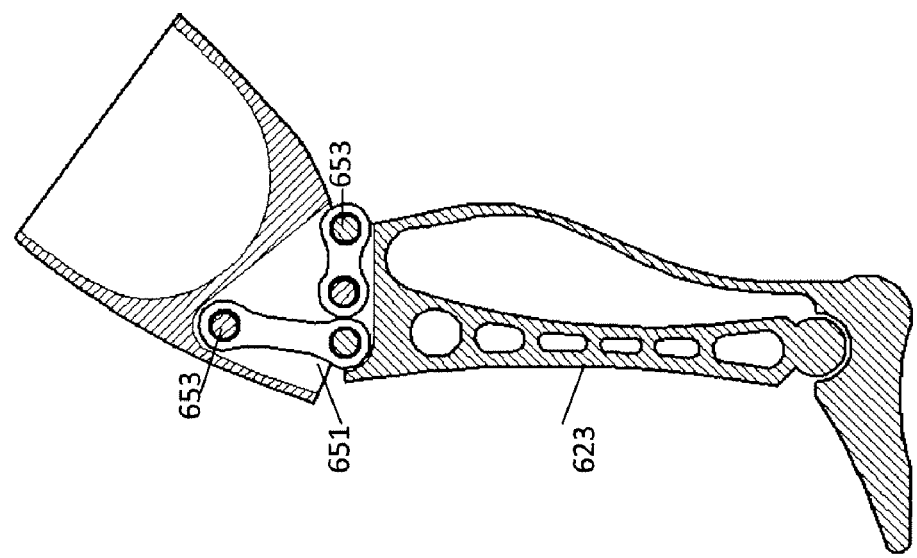
FIGS. 6a and 6b are cross sectional views of an embodiment of the knee, lower leg and foot of a prosthetic leg.
Figure 6A:
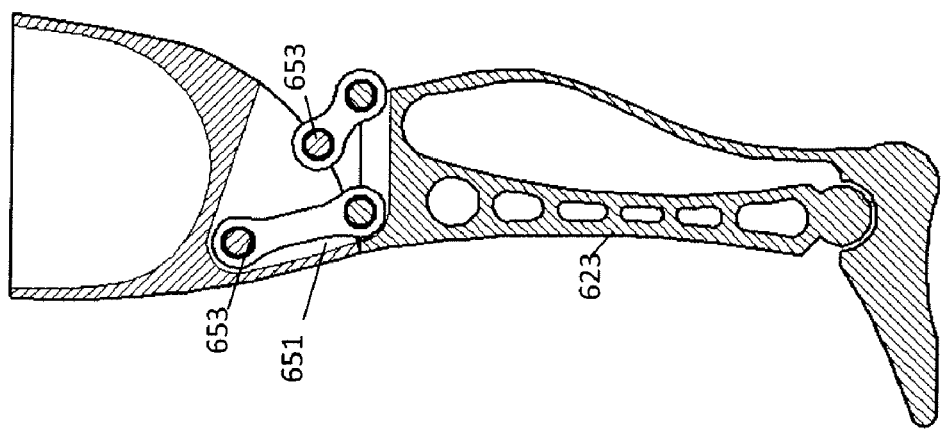

FIGS. 6a and 6b are cross sectional views of a multi-link embodiment of a knee 651 portion of the prosthetic leg 623 in different positions. With reference to FIG. 6a, the upper leg is aligned with the lower leg and the knee 651 is in the straight position. FIG. 6b illustrates the knee 651 in a partially bent position. The circular features 653 represent rods which have circular cross sections and rotate within cylindrical holes. The rotation of the knee 651 allows the leg to rotate.

In the straight position shown in FIG. 6a, the lower leg may be locked in place so that a user can apply weight to the leg without having it bend and collapse. This feature is particularly useful when the user is walking up or down an inclined surface or steps. The locking mechanism can be a mechanical device such as a locking device such as a screw or a lever. Alternatively, the locking mechanism can be a device that responds to the user's movement. For example, the knee 651 may lock when the foot is on the ground and the leg is straightened. The knee 651 may unlock when the user lifts the foot and moves the knee forward to initiate a forward walking motion.

FIG. 7a illustrates another embodiment of the inventive prosthetic leg 951 which has an automatic knee locking mechanism. A large diameter rod 961 is coupled to the bottom of the upper leg 953 and extends across the width of the knee. A "C" clamp 971 is coupled to the lower leg 955 with one end coupled to the front member 957 and the opposite end coupled to the rear member 935. With reference to FIG. 7a, the lower leg 955 is shown in the upright position. A normal amount of compressive force may be applied to the rear member 935 which causes the C clamp 971 to tighten around the rod 961. There is a normal gap between the ends of the C clamp 971. Thus, the lower leg 955 is held in place when the user is standing upright and can be positioned by the user.

FIGS. 7b, 7c and 7d show the lower leg 955 when the user is walking. When the user steps forward, the rear member 935 is compressed as the foot rotates forward as shown in FIG. 7b, the C clamp 971 is tightened around the rod 961 which locks the lower leg 955 in place and provides support for the user as weight is transferred to the lower leg 955. Thus, the ends of the C clamp 971 are much closer together. As shown in FIG. 7c, as the user moves forward, the lower leg 955 rotates over the foot 947 and the heal lifts from the ground. When the lower leg 955 is rotated forward, the rear member 935 is stretched. The ends of the C clamp 971 are spread apart and the C clamp 971 is loosened which allows the lower leg 955 to rotate around the rod 961. When the lower leg 955 is lifted as shown in FIG. 8d, the rear member 935 is not under compression and does not lock the C clamp 971 in position around the rod 961. Thus, the lower leg 955 may rotate or may be movable by the user to position the lower leg 955 if necessary. In FIG. 7d, the lower leg 955 is lifted and rotated back to mimic the movement of a human leg. As the leg rotates forward, the lower leg 955 will rotate forward to the straight position shown in FIG. 7b and the described step process is repeated.

Figure 8:
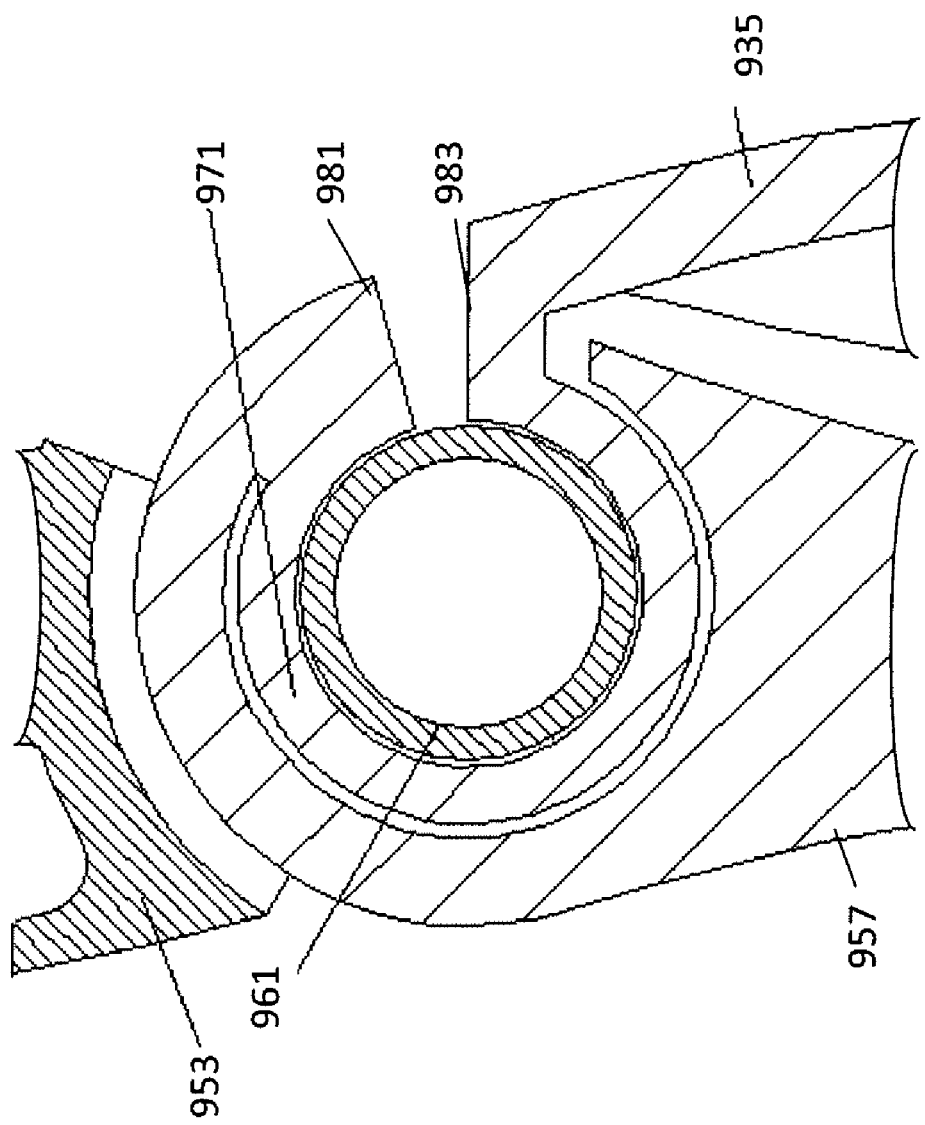
FIG. 8 illustrates a cross sectional view of the locking knee.

With reference to FIG. 8, a more detailed illustration of the knee is illustrated. The upper leg is coupled to the cylindrical rod 961 which is surrounded by the C clamp 971. The C clamp 971 has a first end 981 coupled to an outer structure that extends around the top and front of the knee and is attached to the front member 957 of the lower leg. The second end 983 of the C clamp 971 is coupled to the rear member 935 of the lower leg 955. The configuration of the C clamp 971 also provides some cushioning when the user walks. The C clamp 971 may only be coupled to the lower leg by the first end and the second end. Thus, the C clamp 971 can flex as the weight of the user is applied to the cylindrical rod 961 from the upper leg 953.

Although the "C" clamp is illustrated as a flexible structure made from a plastic material, it is also possible to use a strap brake which is a thinner material that replaces the C clamp but functions in the same way. The strap brake is tightened around the cylindrical rod when the heal contacts the ground and the rear member is compressed. When the user moves forward over the front of the foot the heel is lifted and the rear member is in tension which releases the tension of the strap brake around the cylindrical rod which allows the lower leg to rotate.

Because the entire prosthetic leg may be made of a single material, some portions of the material areas will slide against the same material. Because the materials have the same hardness, both pieces will tend to wear. Without a self lubricating material, the sliding can result in wear and damage to the sliding surfaces within the foot and knee. This can result in friction as the smooth sliding surfaces are damaged which will alter the movement of the knee and foot and may eventually cause the leg to fail.

In an embodiment, the material used to fabricate the prosthetic leg is a self lubricating plastic material that can slide against itself without damage. It is also possible to place a lubricating material such as grease, graphite or Teflon at the sliding areas to reduce the sliding friction. A lubricant can also be used between the components to reduce sliding friction and reduce erosion of the surfaces. In an embodiment, the sliding surfaces may have recesses or porous areas that are impregnated with a lubricating material. The lubricant can be replaced as it is consumed.

In other embodiments, additional components can be added to the prosthetic leg so that the components do not slide against the same material. In an embodiment, bushings or bearings can be added to the leg at the points of rotation. The bushings may be made of lubricious materials such as, stainless steel, ceramic, Delrin or Teflon. In other embodiments, bearings are used. The bearings may be sealed units with roller, needle, ball bearings or any other type of bearing. The bearing material may be ceramic, metal or plastic. Known mechanisms may be used to retain the bushings and/or bearings between the sliding surfaces.

Figure 9:
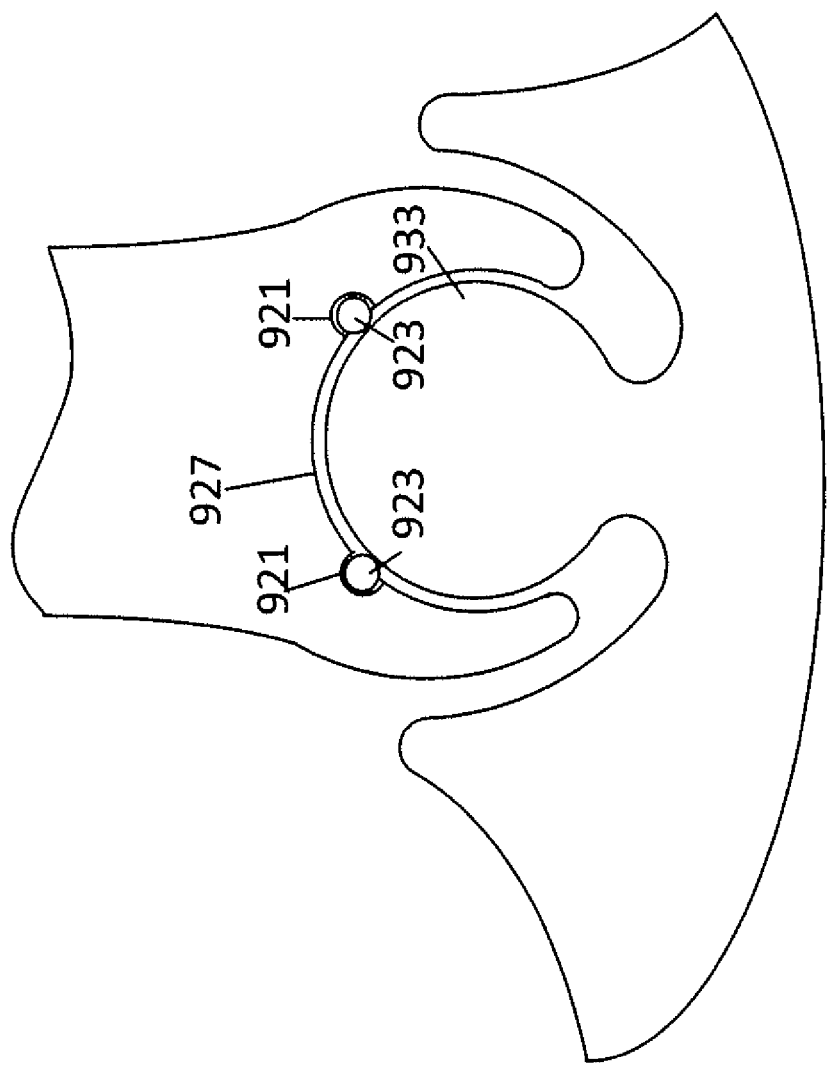
FIG. 9 illustrates a cross sectional view of an embodiment of an ankle.

With reference to FIG. 9 a detailed illustration of the ankle is shown. In an embodiment the sliding concave (or convex) surfaces can have recessed areas 921 that provide voids, holes or indentations that retain the bearings 923 in the desired positions. The bearings 923 can be balls, cylindrical rollers or any other type of rotating bearing structures or sliding bushing structures. These recessed areas 921 can function as bearing races that keep the bearings 923 or bushings evenly distributed around the sliding surfaces. In this embodiment, the bearings 923 are spherical and the recessed areas 921 are circular, cylindrical or semi-spherical in shape and formed in the concave surface 927. The bearings 923 rotate against the outer convex spherical surface 933 of the ankle that is coupled to the foot (not shown).

The described bearing system may also improve the manufacturability of the inventive prosthetic leg. In the preferred embodiment, the components are fabricated simultaneously using a rapid prototyping machine. While the parts can easily be fabricated simultaneously, it can be difficult to create parts such as ball and sockets that are smooth and have a very tight spacing. When bearings are used in the sliding leg components, the spacing is much less critical. The sliding components can be fabricated simultaneously with a larger gap between the moving components. After fabrication, the bearings can be inserted between the components. The bearings provide a smooth sliding mechanism and also tighten the fit between the sliding components. If the bushings or bearings wear out, they can be replaced so the leg can be repaired. In contrast, it can be much more difficult to repair a sliding fit connection if the sliding surfaces have been eroded away.

In an embodiment, the CAD system can include a graphical user interface (GUI) that allows the prosthetic designer to easily change the appearance of the leg and fairing. The GUI may be a special, custom, proprietary application, or it may simply be a CAD model that is built inside Pro/E. The GUI can have controls that allow the prosthetic leg to be viewed with a specific color that preferably matches the user's skin color but may also be any other color.

When the prosthetic designer completes the designs of the prosthetic leg, the design data produced by the CAD software can, when coupled with the unique data of the mirrored scan data taken from the sound side leg, be used to create a unique and custom fabricated leg. Rapid prototyping is a general category of systems that uses digital design data and software to fabricate the components from various types of materials including metals and plastics. These machines most often use an energy beam that is deflected across a bed of liquid or powdered material. The exposure to the energy beam causes the material to fuse together and harden. These fabrication machines are able to create all custom prosthetic limb components.

In order to fabricate the prosthetic leg components with the rapid prototyping machines, the CAD design data must be modified. The normal CAD design data for a component is converted into many parallel cross sections of vector data that extend along the length of the component. The data transmitted between the CAD software and the fabrication machine approximates the shape of the component cross sections through many connected triangular facets. Smaller facets produce a higher quality surface but require more time to calculate and can create very large manufacturing data sets. The output of the CAD design program can be a standard STL file that is an export option, similar to a JPG export or any other file format.

The vector data for the component cross sections is read by a rapid prototyping scanner controller that converts the vector data to movement information which is sent to the energy beam scanhead. In a laser beam embodiment, the rapid prototyping machine includes a scanhead having two mirrors that deflect the laser beam in the X and Y coordinates over a bath of liquid or powder material. The fabrication information is then used to control the print head cross section to create each component cross section successively. The scanhead controller reads the fabrication data and causes the print head to expose successive layers of liquid, powder, or sheet material to precise patterns of laser light. Once the layer is completely formed, the component is moved into the bath so a thin layer of the material covers the previously formed layer. The process is repeated many times with new layers formed and fused to the previously formed layers. In an electron beam embodiment, an electron beam is deflected over a bath of material in the X and Y coordinates with magnetic fields. The component cross sections are sequentially formed until the component fabrication is completed.

The primary advantage to additive fabrication rapid prototyping is the ability to create very complex shapes and geometric features such as the internal framework and exterior surfaces of the prosthetic leg. A light weight and strong prosthetic limb can be made with a rapid prototyping machine from plastic materials such as photopolymers. An additional benefit of rapid prototyping is the ability to create complex, interlinked and assembled parts in one run. In contrast, traditional means used by the prior art required the individual manufacture many parts, followed by an assembly of the parts. Thus, the assembly can add significant costs, even though the individual parts may themselves cost very little to produce.

The rapid prototyping process can be applied to various materials including thermoplastics, photopolymers, metal powders, eutectic metals, titanium alloys and other materials. Because the inventive prosthetic leg is intended to be inexpensive, the preferred material is a thermoplastic material. Examples of some suitable rapid prototyping machines include: laser sintering machines by EOS GmbH, electron beam sintering machines by Arcam AB and laser stereo lithography machines and selective laser sintering machines by 3D Systems Corp. Similar fabrication processes are known by the names: additive manufacturing, rapid manufacturing, layered manufacturing, 3D printing, laser sintering, electron beam melting (EBM), etc. All of these fabrication processes use a similar operating principle of scanning an energized beam over a bath of material to solidify a precise pattern of the material to form each layer until the entire component is complete.

Another possible fabrication process is fused material deposition (FDM). FDM works on an "additive" principle by laying down material in layers. A plastic filament or metal wire is unwound from a coil and supplies material to an extrusion nozzle which can turn on and off the flow. The nozzle is heated to melt the material and can be moved in both horizontal and vertical directions by a numerically controlled mechanism, directly controlled by CAD software. In a similar manner to stereo lithography, the model is built up from layers as the plastic hardens immediately after extrusion from the nozzle.

As discussed above and illustrated in FIGS. 6a and 6b, the knee 651 may include a plurality of rotatable linkages that are coupled to rods 653 that rotate within holes. Current rapid prototyping machines are capable of forming assemblies with rods within holes simultaneously. However a small gap between adjacent components is required to prevent the rod from being fused to the hole during the fabrication process. In order to provide a sufficient gap as well as a tight tolerance, the rod and corresponding hole may not be perfectly circular in cross section.

Figure 10A:
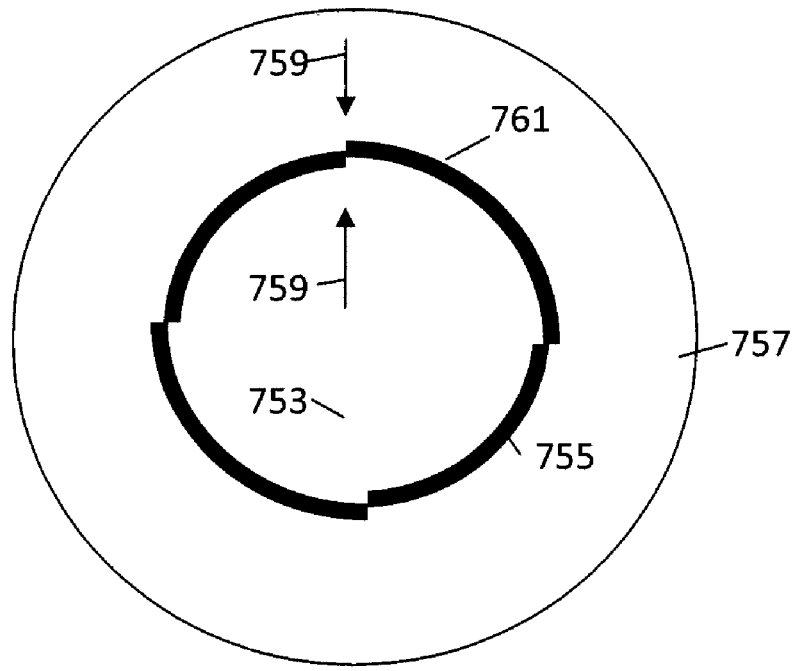
FIGS. 10a and 10b are cross sectional views of an embodiment of a rod and hole assembly.

With reference to FIG. 10a a cross sectional view of a rod 753 and a hole 755 in a linkage component 757 are shown. The rod 753 has two opposite 90 degree section may be created with a larger radius and two other 90 degree sections may be created with a smaller radius. The difference between the larger radius and the smaller radius may be the gap 761 required by the rapid prototyping fabrication process. Once fabricated, the rod 753 has a loose fit within the hole 755 due to the gap 755. The original orientation of the rod 753 and the hole 755 are indicated by the arrows 759 on the upper side which are aligned.

Figure 10B:
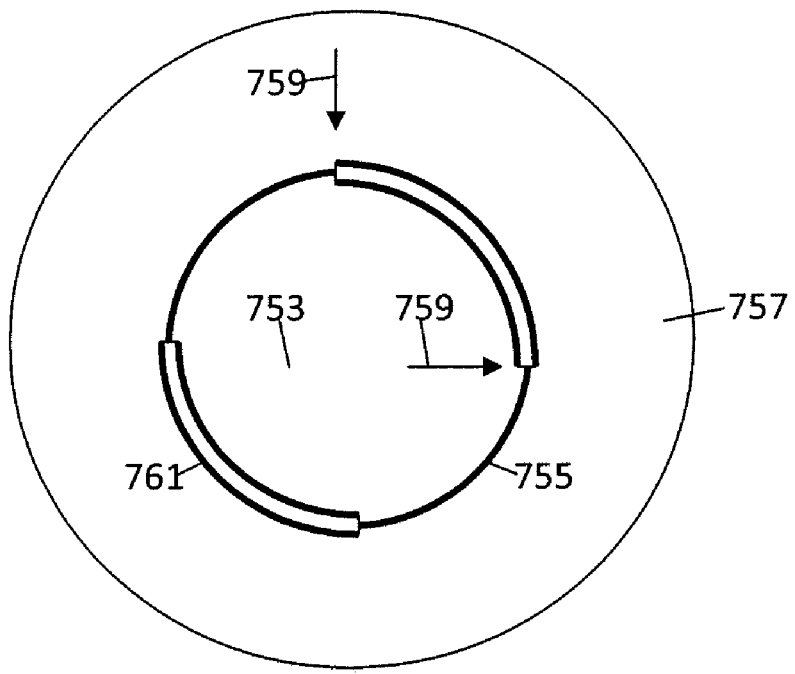

With reference to FIG. 10b, after fabrication, the rod 753 may be rotated within the hole 755 so that the arrows 759 are offset by 90 degrees. The larger radius section of the rod 753 is adjacent to the smaller radius of the hole 755 with a tight gap that still allows free sliding rotation. This creates two sliding surfaces between the rod 753 and hole 755 that are very closely fit and two other adjacent surfaces that are separated by a much larger gap 761. As discussed above, this method for forming tight tolerance sliding surfaces may not be required if bearings are inserted into indentations in the sliding surfaces.

Figure 11:
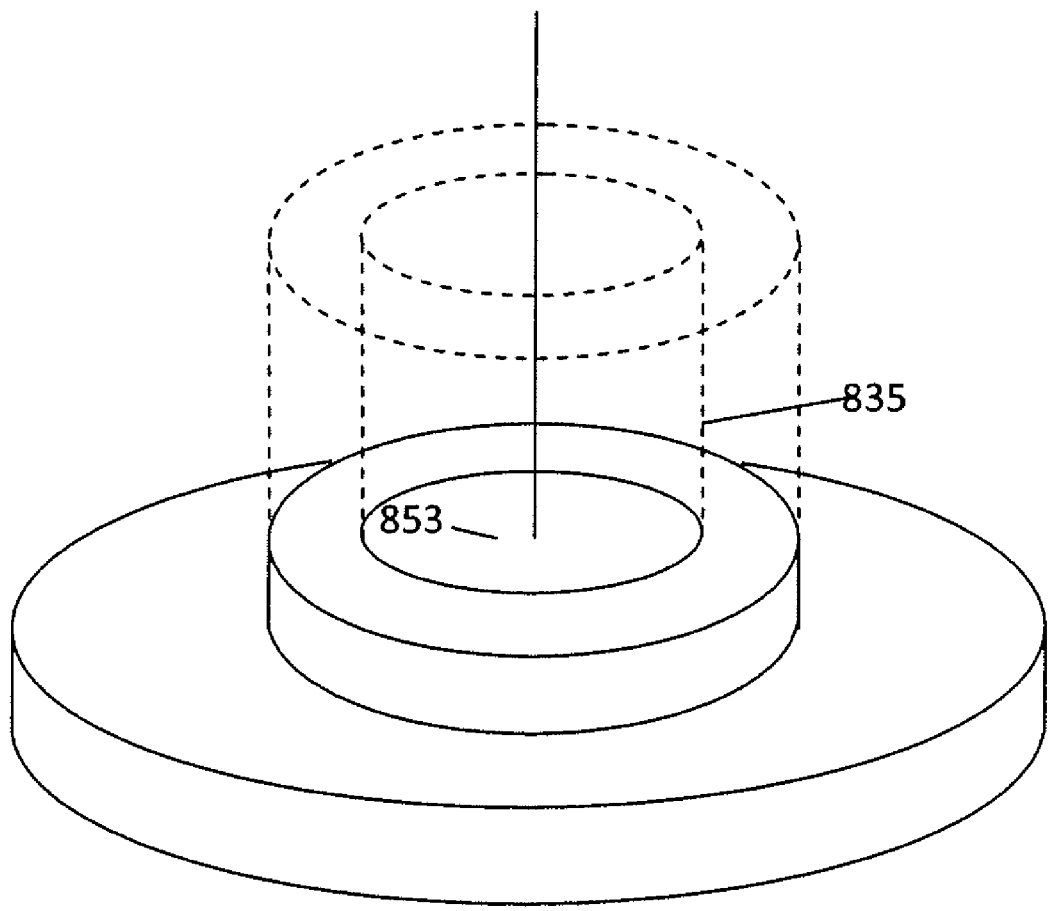
FIG. 11 illustrates a partially fabricated rod and hole assembly.

With reference to FIG. 11, the fabrication of a rod 753 and hole 755 using a rapid prototyping machine is illustrated. The fabrication is most precisely controlled when the rod 853 and hole 855 are substantially perpendicular to the sequential planes of deposited material. The described rod 753 and hole 755 configuration allows the rapid prototyping machine to be used to create a knee having rotating components with tight tolerances.

In an embodiment, the prosthetic leg may be formed with the knee in a bent position. An angle of 180 degrees represents a straight leg. In an embodiment, the upper leg and the lower leg may be bent at an angle of about 270-350 degrees with the rods and holes of the linkages fabricated with the required gap in the manner described above. After fabrication, the knee can be rotated to the normal functional range of about 180 to 260 degrees. In the normal operating position, the rods and holes of the knee linkages may have close tolerance fits resulting in a smooth rotating prosthetic knee. A mechanism may prevent the leg from rotating beyond the 260 degree bend where the rods and holes of the knee linkages will have a large gap. This close fitting embodiment may be required when other types of bearings or bushings are not used to keep the components in a tight rotational configuration.

Figure 12:
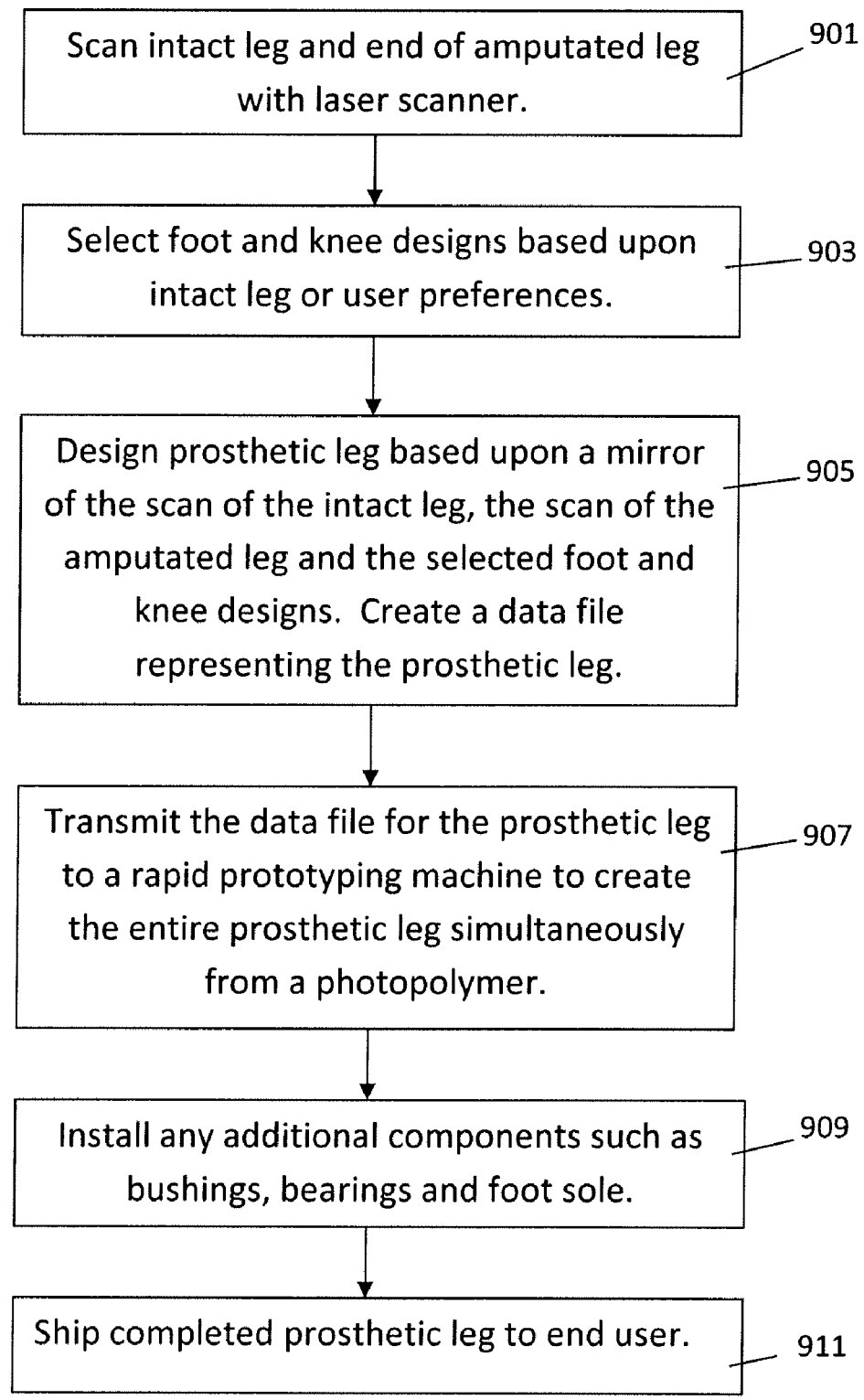
FIG. 12 is a flowchart for the design, fabrication and delivery of the prosthetic leg using scanned intact leg surface data.

The sequential process by which the inventive prosthetic leg can be fabricated is represented by FIG. 12. It an embodiment, a prosthetic designer scans the patient's intact leg and end of the amputated leg with a laser scanner 901. Mirror image data is created from the scan of the intact leg and reversed surface is created from the scan of the end of the amputated limb. The foot and a knee are integrated into the prosthetic leg based upon a pre-designed program 903. The prosthetic leg is then designed using the mirror image data to create an exterior surface, the reversed surface to create a socket. The locations of the knee and foot are identified and the knee and foot are incorporated into the leg design in positions that match the intact leg. A prosthetic leg design is then converted into an electronic data file 905. The prosthetic leg data file is transmitted to a rapid prototyping machine which creates the leg in a single fabrication process from a photopolymer material 907. Any additional components are required such as bushings, bearings or foot sole inserts, these components can be installed at the fabricators facilities 909.

The completed prosthetic leg is then shipped to the end user 911. This process allows amputees located in very remote areas to obtain prosthetic limbs. Since digital data can be transmitted on digital media via mail, electronically via cell or satellite, the inventive process greatly improves the design, fabrication and distribution of prosthetic legs.

Figure 13:
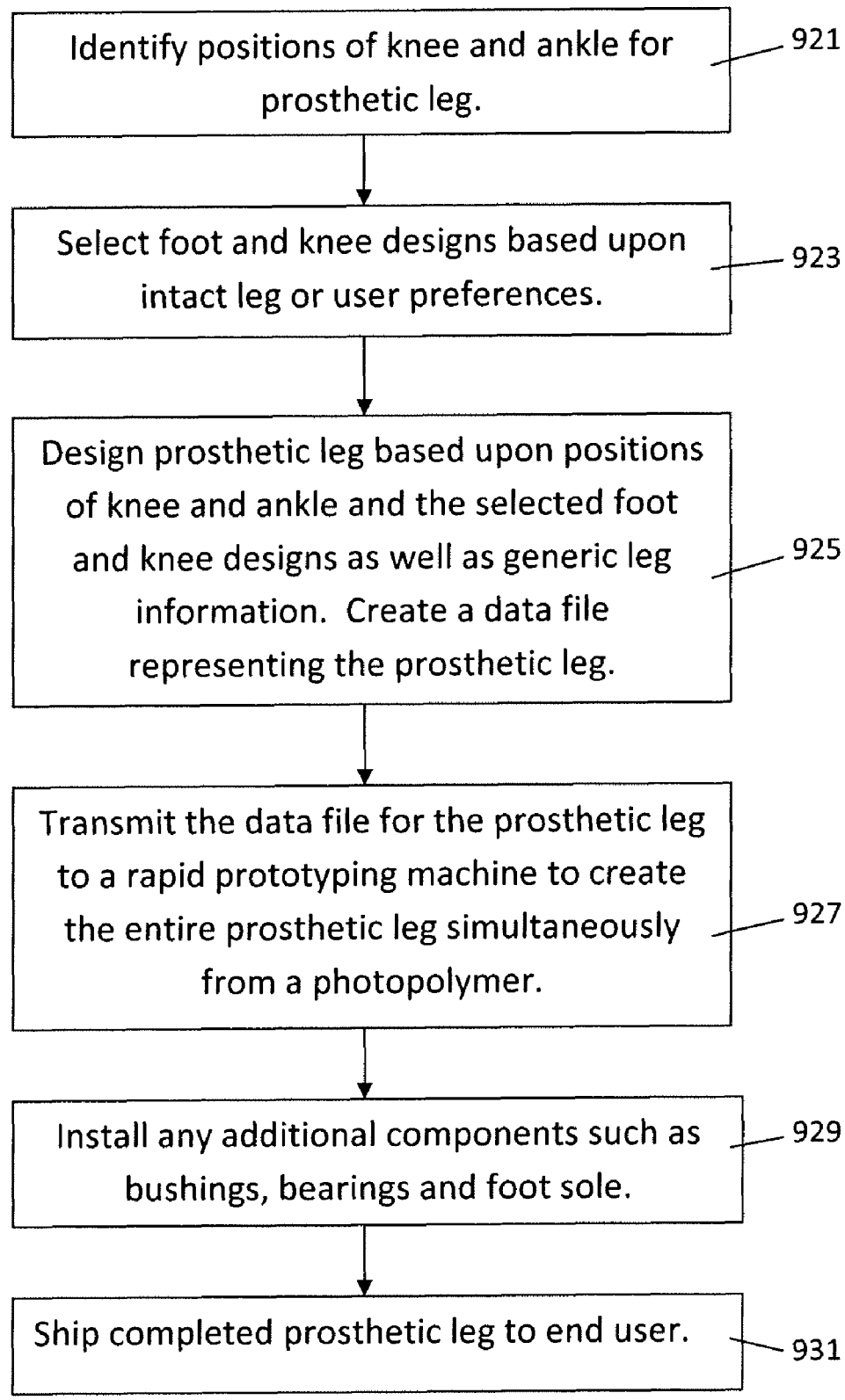
FIG. 13 is a flow chart for the design, fabrication and delivery of the prosthetic leg using generic leg surface data.

In other embodiments, it is possible to use a generic leg that is designed to resemble an intact leg without scanning the outer surface of the intact leg. The sequential process by which the inventive prosthetic leg can be fabricated without the scanned data is represented by FIG. 13. In this method, a prosthetic designer determines the positions of the knee and ankle for the prosthetic leg 921. The surface data for the prosthetic leg is obtained from a generic leg. The foot and a knee are integrated into the prosthetic leg based upon a pre-designed program 923. The prosthetic leg is then designed using the genetic leg to create an exterior surface. The exterior surface can be modified to include measurements taken from the intact leg. For example, the generic leg can be modified to have the same length and width as the intact leg at corresponding vertical positions. The knee and foot are incorporated into the leg design in positions that match the intact leg. A prosthetic leg design is then converted into an electronic data file 925. The prosthetic leg data file is transmitted to a rapid prototyping machine which creates the leg in a single fabrication process from a photopolymer material 927. Any additional components are required such as bushings, bearings or foot sole inserts, these components can be installed at the fabricators facilities 929. The completed prosthetic leg is then shipped to the end user 931.

It will be understood that the inventive system has been described with reference to particular embodiments, however additions, deletions and changes could be made to these embodiments without departing from the scope of the inventive system. For example, the same processes described for designing and fabricating a prosthetic leg can also be applied to the design and construction of a prosthetic arm that can include a socket, an elbow, an elongated member and an artificial hand. Although the prosthetic limbs that have been described include various components, it is well understood that these components and the described configuration can be modified and rearranged in various other configurations.

What is claimed is:

1. A prosthetic leg comprising:
   an upper leg coupled to a socket;
   a lower leg having a front member and a rear member, wherein the front member is substantially rigid and the rear member does not extend forward of the front member and compressive loads for supporting a user of the prosthetic leg are partially distributed to the rear member;
   a knee that is coupled to a lower end of the upper leg and an upper ends of the front member and the rear member that allows the lower leg to rotate relative to the upper leg; and
   a foot having an ankle section with a sliding surface that engages a lower portion of the front member and a heel section that is coupled to the lower end of the rear member;
   wherein the upper leg, the lower leg, and the knee each comprise a series of planar layers that are substantially parallel to lengths of the upper leg and the lower leg and perpendicular to an axis of rotation of the knee.

2. The prosthetic leg of claim 1 wherein the knee comprises a plurality of rotatable linkages.

3. The prosthetic leg of claim 1 wherein the prosthetic leg includes indentations that each partially surround a bearing.

4. The prosthetic leg of claim 1 wherein an outer surface of the upper leg or the lower leg is designed referencing surface data of the generic leg.

5. The prosthetic leg of claim 4 wherein the surface data of the generic leg is modified to match some measurements of an intact leg of the user.

6. The prosthetic leg of claim 1 wherein the foot includes a front portion and a main portion that are coupled by an elastic member that allows the front portion to rotate relative to the main portion.

7. The prosthetic leg of claim 1 wherein the lower leg rotates relative to the foot, a sliding surface of the foot slides against a lower portion of the front member causing a distance between the heal portion and the knee to change and the rear member to be elastically deflected.

8. The prosthetic leg of claim 7 wherein the lower leg rotates forward towards a front portion of the foot, a distance between the heal portion and the knee is increased stretching the rear member and causing a bow of the rear member to flattened.

9. The prosthetic leg of claim 7 wherein the lower leg rotates back towards the heal portion of the foot, a distance between the heel portion and the knee is reduced compressing the rear member and causing a bow of the rear member to increase.

10. The prosthetic leg of claim 7 wherein the lower leg rotates sideways about a center axis of the foot, causing the heel section of the foot to deflect the rear member sideways.

11. The prosthetic leg of claim 1 wherein a spring mechanism of the rear member has a predetermined spring rate.

12. The prosthetic leg of claim 1 wherein a lower end of the front member includes a convex spherical surface that slides again a concave spherical surface coupled to the foot so that the foot may rotate relative to the lower leg.

13. The prosthetic leg of claim 1 wherein a lower end of the front member includes a concave spherical surface that slides against a convex spherical surface coupled to the foot so that the foot may rotate relative to the lower leg.

14. The prosthetic leg of claim 1 further comprising:
   a beam having a convex spherical surface that is coupled to the first end of the beam, a second end of the beam is coupled to the heel section of the foot and a downward force applied to the convex spherical surface causes the beam to bend.

* * * * *